(12) United States Patent
Völker et al.

(10) Patent No.: US 11,207,622 B2
(45) Date of Patent: Dec. 28, 2021

(54) FILTER SYSTEM

(71) Applicant: FIDICA GmbH & Co. KG, Sailauf (DE)

(72) Inventors: Manfred Völker, Blankenbach (DE); Cornelia Schmitt, Sailauf (DE); Reinhart Thomas, Niedernberg (DE)

(73) Assignee: Manfred Volker, Blankenbach (DE)

( * ) Notice: Subject to any disclaimer, the term of this patent is extended or adjusted under 35 U.S.C. 154(b) by 103 days.

(21) Appl. No.: 16/567,171

(22) Filed: Sep. 11, 2019

(65) Prior Publication Data
US 2020/0078716 A1  Mar. 12, 2020

(30) Foreign Application Priority Data

Sep. 12, 2018 (EP) ..................................... 18000728

(51) Int. Cl.
*B01D 35/30* (2006.01)
*B01D 69/08* (2006.01)

(52) U.S. Cl.
CPC ........... *B01D 35/306* (2013.01); *B01D 69/08* (2013.01); *B01D 2201/291* (2013.01)

(58) Field of Classification Search
CPC .................. B01D 35/306; B01D 69/08; B01D 2201/291; B01D 2201/4023; B01D 2201/4061; B01D 2313/025; B01D 2313/06; B01D 2313/13; B01D 63/02; B01D 61/20; B01D 61/30; B01D 61/18; B01D 61/28; B01D 35/303; B01D 35/00; B01D 35/30; B01D 2201/30;

(Continued)

(56) References Cited

U.S. PATENT DOCUMENTS 6,277,277 B1  8/2001  Jacobi et al.
7,217,364 B2  5/2007  Lauer et al.

FOREIGN PATENT DOCUMENTS

AU    744404 B2 *  1/1999  .......... A61M 1/1652
AU    744404 B2    1/1999

(Continued)

OTHER PUBLICATIONS

Search Report, European Patent Office, Application No. EP 18000728, dated Mar. 6, 2019.

*Primary Examiner* — Madeline Gonzalez
(74) *Attorney, Agent, or Firm* — Greer, Burns & Crain, Ltd.

(57) ABSTRACT

The filter system having a filter and a filter holder, wherein the filter is connected to an upper and a lower filter cap, wherein on the circumference of the filter caps a cross-sectionally T-shaped fixing aid is respectively mounted, having a laterally projecting transverse web, which are vertically aligned with each other, wherein on an outer side of the housing of the filter holder two filter fixings are mounted with grooves in which the transverse webs can be suspended, is characterized in that four hydraulic ports project laterally from the filter and/or the filter caps, which are vertically aligned with each other, and that the filter holder has four connection connectors, which can be advanced by an upper and a lower closure mechanism against spring force until they engage in an end position in which the connection connectors are tightly connected to the hydraulic connections.

15 Claims, 5 Drawing Sheets

(58) Field of Classification Search
CPC ............... B01D 2201/29; B01D 35/02; C02F 2201/004; C02F 1/001; A61M 1/1672
USPC ....... 210/435, 459, 463, 473, 232, 236, 282, 210/287, 321.6, 321.78, 321.87, 446, 455, 210/500.23, 240, 235, 645, 646
See application file for complete search history.

(56) References Cited

FOREIGN PATENT DOCUMENTS

| | | | |
|---|---|---|---|
| JP | 2015177973 A | 10/2015 | |
| JP | 2016049177 A | 4/2016 | |

* cited by examiner

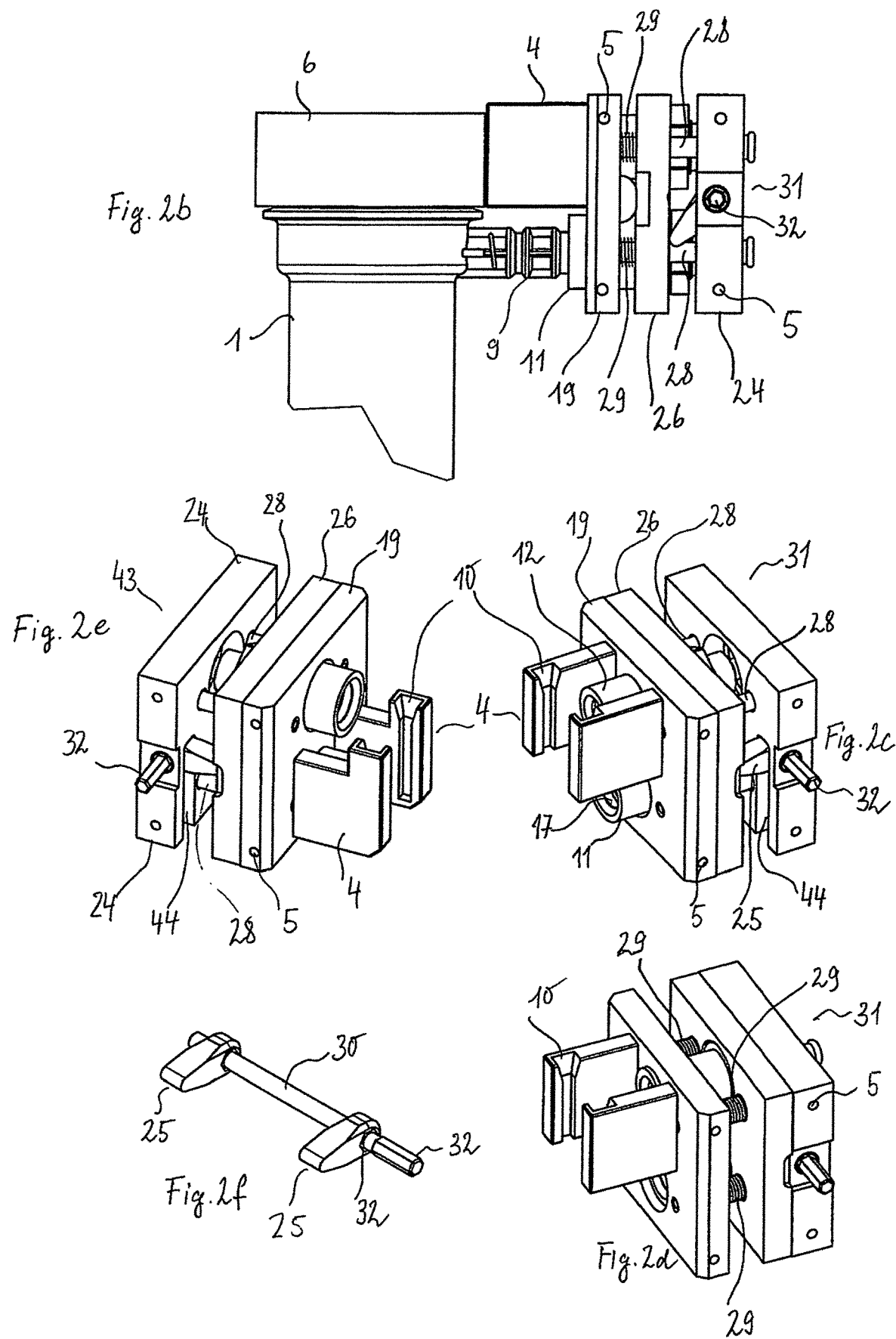

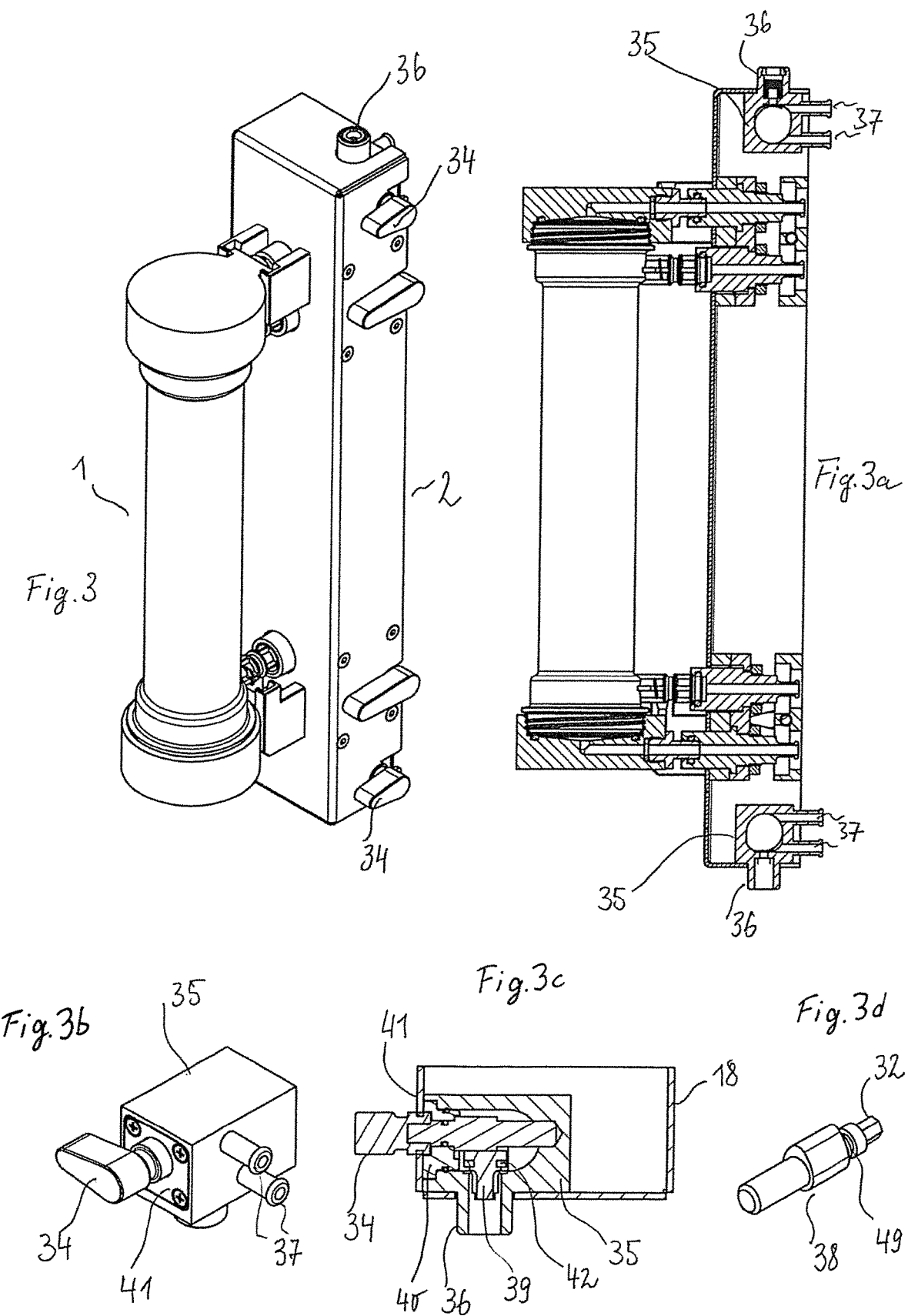

FILTER SYSTEM

FIELD OF INVENTION

The invention relates to the inexpensive sterile or ultrafiltration of liquids to obtain a higher degree of purity, especially from bacterial contamination. In this case, a modified capillary filter can be used, as it is used for example in dialysis. The embodiment and design are not limited to dialyzers, but depending on the requirements, for example, on required filtration volumes, other, for example, larger designs and filter media are possible.

BACKGROUND OF THE INVENTION

Mainly the filters for drinking water treatment are to be used, but also, for example, after exchangers or after waters which were treated by membrane filtration.

The application area extends thus not only to the drinking water treatment, but also from laboratory water, pharmaceutical water, med. techn. water for rinsing solutions up to applications in the hospital.

Filters of this type are not new, but these filters are expensive consumables. The large supply base of dialyzers and their excellent quality in terms of bacterial restraints, as well as the increasing contamination of the water are a basis of this invention.

Disadvantages of the prior art are, in particular, the lack of pressure resistance of filters of the type described above, as well as the lack of a simple, fail-safe and pressure-resistant connection for untrained users in the application areas described above. The given flow cross-sections of the connections should not be affected, i.e. not minimized or reduced.

SUMMARY OF THE INVENTION

The object to be solved is therefore to develop a cost-effective, pressure-resistant filter without flow-minimizing connections, which is safe and easy to connect or replace.

For this purpose, the dialyzer receives flameproof caps, each with a hydraulic connection connector. The connection connectors of the two caps run vertically in line with the hydraulic connections molded onto the dialyzer housing. The thereby modified filter is connected to a filter holder to be described later. These together form the filtration system. The filter holder itself can, for example, be fixed or mounted on a wall in a stationary manner under table or water treatment devices, or as an additional filtration extraction unit in the laboratory.

Main functional units of the filtration system are the elements of a closure mechanism in the filter holder, which creates a secure hydraulic connection between filter and filter holder, as well as the elements of a mechanical filter fixing in the filter and filter holder, which allow both the error-free arrangement of the filter in the filter holder, as well as initially the mechanical connection and thus the positive hydraulic connection between the filter and filter holder.

For the mechanical connection, the filter, which has T-shaped fixings on both caps, is inserted into the grooves of the fixing on the filter holder until the stop.

To facilitate and for targeted introduction of the filter, the fixings on the filter holder are designed such that inexperienced users can perform the filter change. To this end, upwardly widening V-shaped grooves and a slightly longer lower filter fixing on the filter holder serve, in order to attach the filter initially to one side, at the lower end.

The two fixings on the filter holder are part of the upper and lower closure mechanism.

The hydraulic connection is made by turning the connecting lever of the lower as well as the upper closure mechanism.

For this purpose, two plungers are mounted against rotation on a rotating shaft of the connecting lever. These plungers press the hydraulic connection connectors to their respective counterparts of the filter.

The plungers at the upper and lower closure mechanism are positioned doubly in their end position and are in the engaging position slightly above 9 o'clock and cannot reset themselves due to the rotation angle and the fixings.

The plungers are fixed on the one hand by guiding in a gap which leads laterally and limits the rotation angle beyond 9 o'clock, as well as by a mechanical engaging position which is supported by spring pressure.

In order to compensate for dimensional deviations, in particular the distance dimensions or angular dimensions of the four vertically arranged connection connectors of the filter, two of the four counterparts, the two middle connection connectors on the filter holder are supported with play by a circumferential annular gap. However, all four connectors of the filter holder holder can be stored easily.

All the connectors on the filter housing seal their connectors on the circumference of the filter, so there are no cross-sectional reductions in the hydraulic connections. In order to open, the connection levers of the upper and lower closure mechanism are turned back, whereby the connection connectors on the filter holder are returned by spring force and the filter can be removed from the fixing.

This substantially fulfills the object described at the outset.

In order to avoid the escape of liquids, it is possible to introduce valves into the housing of the filter holder holder. This embodiment is illustrated in the following descriptions of the figures.

Since the filtration performance of these filters is limited, it is possible to pass on a message or trend display to technology or users by adding a quantity or flow monitoring and their various configurations with regard to signal transmission. To increase filtration performance, filtration systems of this type can also be connected in parallel and serially.

BRIEF DESCRIPTION OF THE DRAWINGS

FIG. 1a is a perspective view of a filter.
FIG. 1b is a perspective view of a filter holder.
FIG. 2b is a profile view of a closure mechanism in middle position.
FIG. 2c is a perspective view of an upper closure mechanism in the connected state.
FIG. 2d is a perspective view of an upper closure mechanism in a relaxed form.
FIG. 2e is perspective view of a lower closure mechanism.
FIG. 2f is a perspective view of a shaft.
FIG. 3 is a perspective view of a filter holder having a locking lever.
FIG. 3a is a cross-sectional view of a closure unit without a valve body.

FIG. 3b is a perspective view of a closure unit.

FIG. 3c is a cross-sectional view of a closure unit.

FIG. 3d is a perspective view of an eccentric shaft.

DETAILED DESCRIPTION OF PREFERRED EMBODIMENTS

Figure 1:
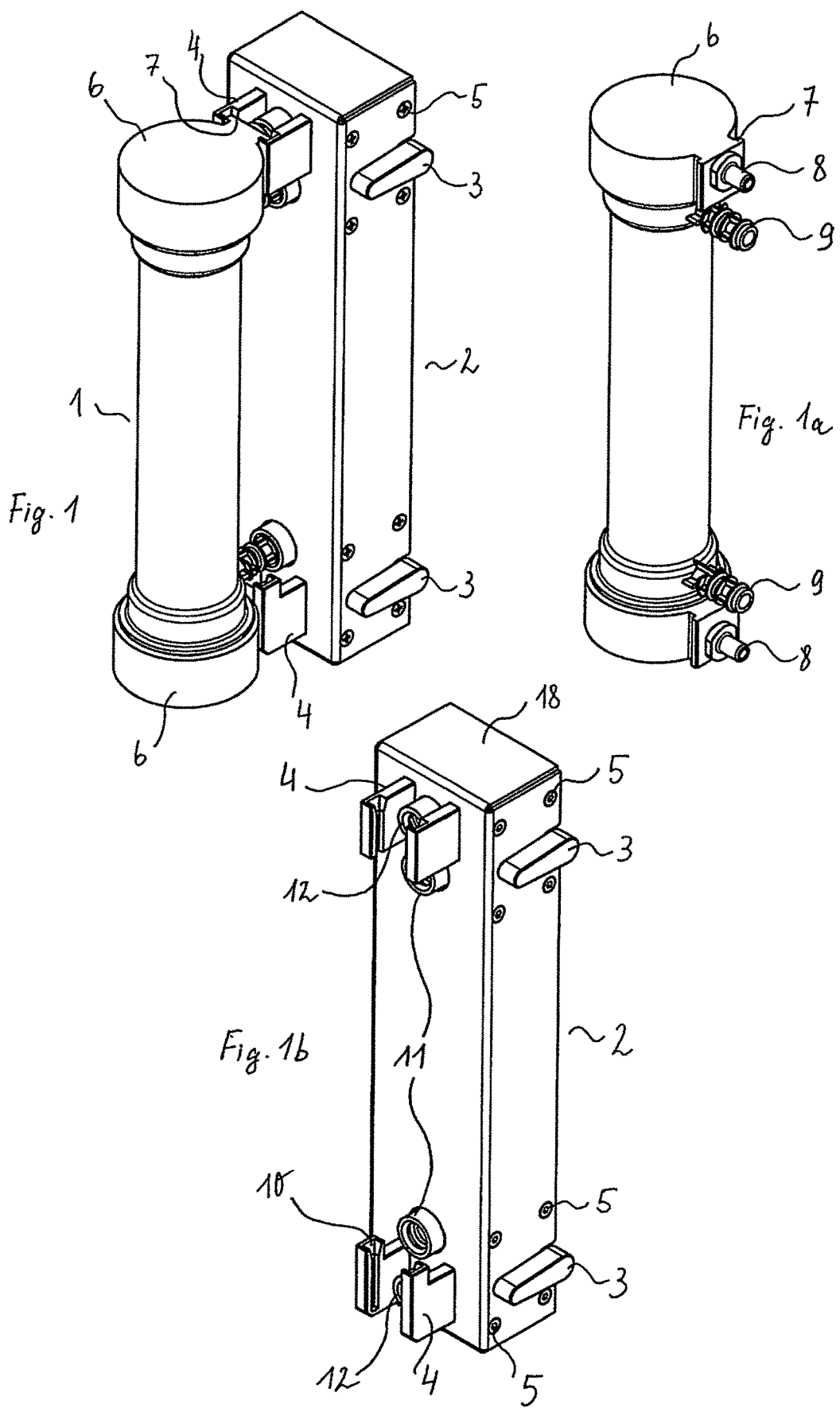
FIG. 1 is a perspective view of a filter system.

FIG. 1 shows a filter system consisting of a hollow fiber filter 1 and a filter holder 2. The hollow fiber filter 1 is screwed to the two filter caps 6. The filter caps are designed laterally T-shaped such that the filter can be hooked into the outer filter fixing 4 of the filter holder 2. On the side of the filter holder 2 are connecting levers 3 that can be mounted both on the left and the right side on the filter holder 2 such that three mounting positions, left, right, center of the filter holder 2, are possible.

FIG. 1 a shows the T-shaped fixing aids located on the filter cap with which the filter is suspended mechanically in the outer filter fixing 4 of the filter holder. The filter itself has two hydraulic connections 9. At the filter caps 6, hydraulic connections 8 are also attached. Depending on the filter design and size, the connections 9 can also be arranged in the respective lower or upper filter caps 6.

FIG. 1b shows the filter holder 2 with the two connection levers 3 with which the filter assembly and the closure mechanism later to be described is operated. On the filter holder itself, the outer filter fixings 4 are attached with their funnel-shaped widened groove 10, in which the fixing aid 7 of the filter is inserted. The lower outer filter fixing has an L-shaped extension upwards in order to facilitate the introduction of the filter 1. Also, the position of the connection connectors 11 and 12 is apparent from the drawing.

Figure 2:
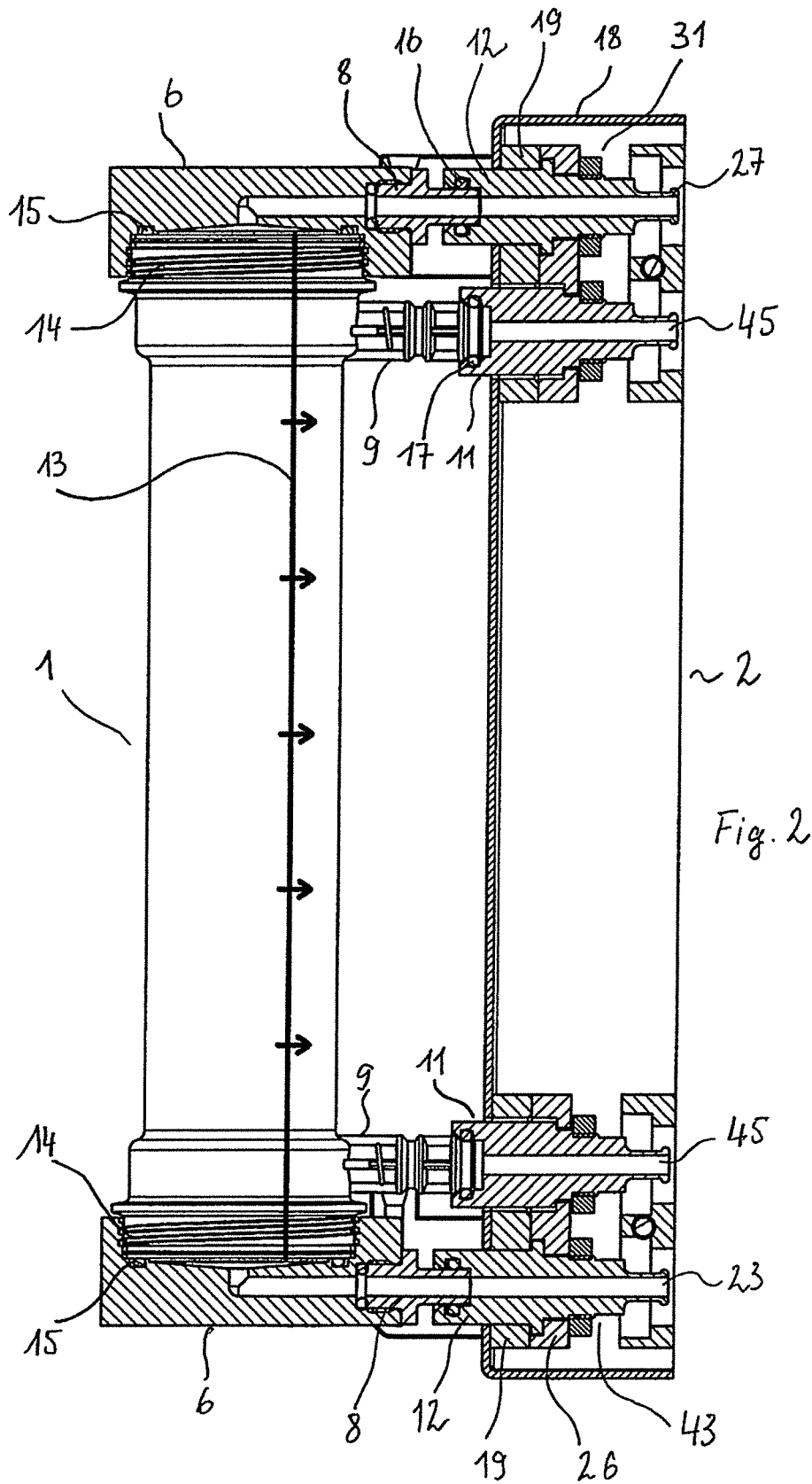
FIG. 2 is a cross-sectional view of a filter system.

FIG. 2 shows the hydraulic connection of the filter system in section.

For example, via connection 23, which is designed here as a hose nozzle, liquids are fed to the filter membrane/capillary 13. The embodiment of the connections 23, 45, 27 shown here can also be replaced by threaded connections.

In a dead-end filtration, connection 27 is closed, or connection 27 is used as a venting, circulating or residue outflow.

The filtrate is removed at the connections 45. Depending on the filtration requirements, the primary and secondary sides of the filter 1 are exchangeable, such that the previously described function of the connections is reversed.

The filter caps 6 are screwed by means of the thread 14 onto the filter 1 such that the connections 8 and 9 are vertically aligned. The filter caps 6 are sealed frontally with the sealing ring 15 against the environment. For additional anti-rotation of the thread 14, there is the possibility (not shown) of locking in the form of a circumferential web which engages in a groove. The groove and webs are optionally executable on the filter or cap.

In the filter holder housing 18 is the upper closure mechanism 31 and the lower closure mechanism 43, wherein these have the connection connectors 11 and 12 sealingly introduced in the respective counterparts of the filter 8 and 9.

Figure 2A:
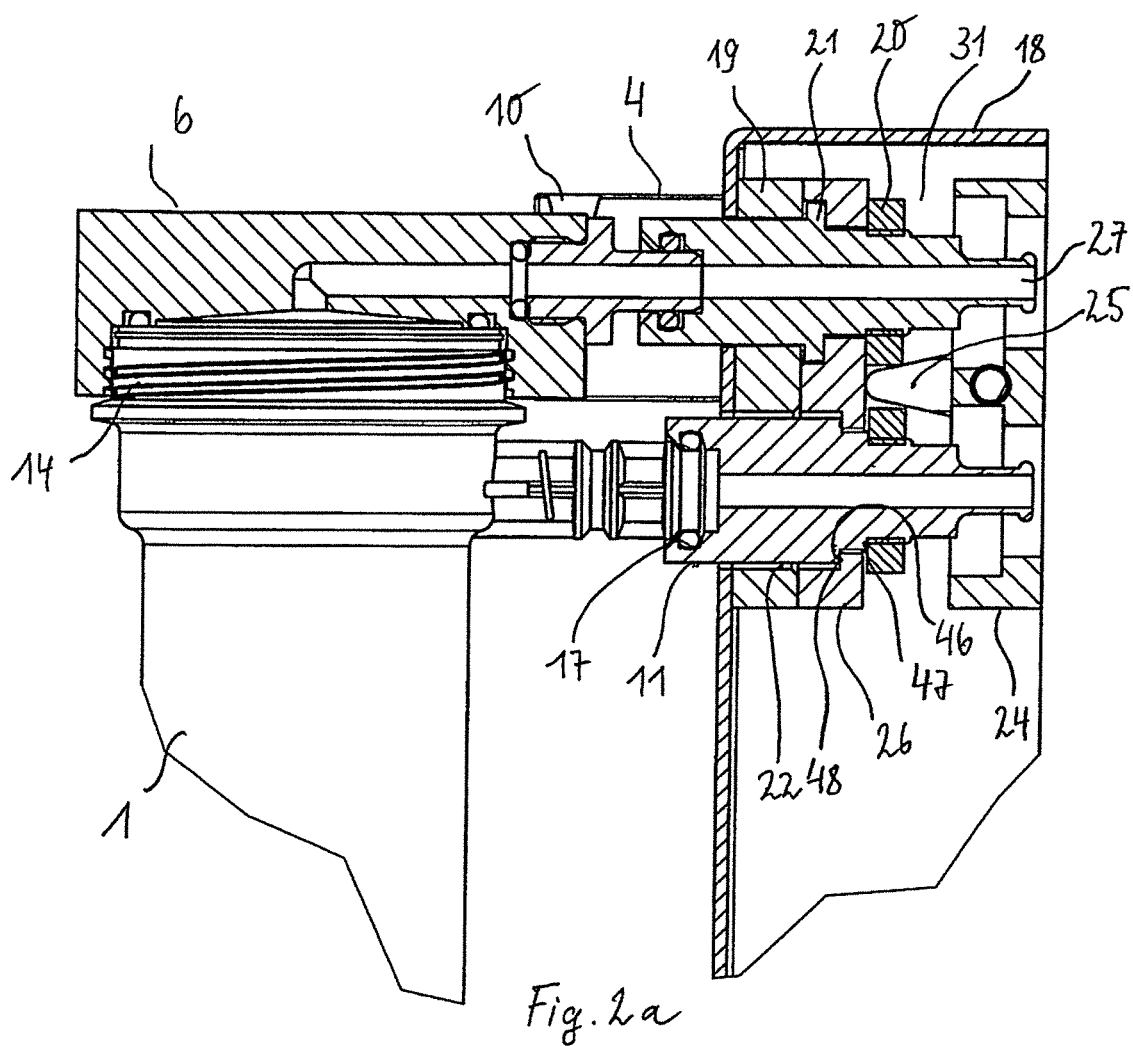
FIG. 2a is a cross-sectional view of a closure mechanism.

FIG. 2a shows, for example, the upper closure mechanism 31 in the connected state with the filter 1.

The closure mechanism 31/43 is designed in three parts and consists of an abutment and guide plate 24 from the connector carrier plate 26 and a front fixing plate 19.

With the connector carrier plate 26, the connectors 12, 11 are mechanically connected. The connector 12 is seated with a flange in a circular pocket 46 and is fixed to each other with a nut 20, the connector 11 is also seated in a circular pocket 46 of the carrier plate, however, the fixing of the nut 20 is limited by an oblique stop 47, and additionally the connector 11 can easily compensate tolerances with the annular gap 22. The tolerance-compensating design and installation position is also possible for connector 12.

FIG. 2a shows the position of the plunger 25 such that the connector carrier plate 26, with connector connections 11 and 12 are brought into closure with the counter connectors of the filter 8 and 9.

FIG. 2b shows the closure mechanism 31 in the middle position.

The three-part closure mechanism 31, 43 is held by four guide pins 28 at a distance. On this guide pin, the connector carrier plate 26 slides during the movement process. The connector carrier plate is brought into its connection position by means of the plunger 25 and pushed back after turning back the plunger 25 via the return spring 29 in its initial position.

The position of the closure mechanism 31, 43 in the filter holder 2 is determined by the attachment 5 in the filter holder housing 18.

FIG. 2c shows the upper closure mechanism 31 in the connected state, while the connection connectors 11 and 12 are pushed forward. The connector carrier plate 26 abuts the front fixing plate 19, the plunger 25 is slightly lifted clockwise above 9:00 o'clock. In this case, the slightly rounded front end of the plunger 25 is located in a recess (not shown here) of the connector carrier plate 26. The four springs 29, which are almost set to block, of each locking mechanism press the plate 26 against the plunger 25 and thus ensure form-fitting.

The springs 29 can dive into annular round cuts (not shown) of the plate 19/26. The plungers 25 press on both sides of the plate 26 and are held in the guide groove 44 such that both an over-rotation upwards and a lateral displacement is not possible.

FIG. 2d shows the closure mechanism 31 in a relaxed form, while the four springs 29 press the connector carrier plate 36 in its final position.

FIG. 2e shows the lower closure mechanism 43 with the funnel-shaped upwardly extending fixing aid 4 in the closed state.

FIG. 2f shows the shaft 30 on which the plungers 25 are pushed to prevent rotation, here, for example, a hexagon was selected as anti-rotation, wherein any other form of anti-rotation, for example square, is also possible.

The outer connection for the connection lever 3 is likewise designed with an anti-rotation 32. The connection lever 3 has an inwardly leading collar having a circular groove into which a cutout of the housing 18 engages. A removal of the connection lever 3 with mounted closure mechanism 31/43 is therefore not possible.

FIG. 3 shows a filter holder having the locking lever 34 and threaded connections 36 with which the filter system can be connected to a domestic or drinking water installation.

FIG. 3a shows, for example, the closure unit 35 in section without valve body. The locking unit 35 may be required to prevent water leakage during filter replacement.

FIG. 3b shows the closure unit 35 in perspective.

FIG. 3c shows the closure unit 35 in section. Via the connection 36, liquid can be connected for input or output, wherein by means of the closure lever 34 the eccentric shaft 38 is rotated such that the valve tappet 39 closes the water input or output, respectively, with the seal 42. The connections 37 are each to be simplified in parallel in a further tubing.

FIG. 3d shows the eccentric shaft 38 in perspective.

| | |
|---|---|
| 1. | Hollow fiber filter |
| 2. | Filter holder |
| 3. | Connection lever |
| 4. | External filter fixing |
| 5. | Attachment connection mechanism |
| 6. | Filter caps |
| 7. | Fixing aid |
| 8. | Filter connection filter cap |
| 9. | Filter connection housing |
| 10. | Filter intake groove with funnel-shaped opening |
| 11. | Connection connector filter housing |
| 12. | Connection connector filter cap |
| 13. | Filter capillary/membrane |
| 14. | Filter thread |
| 15. | Cap seal |
| 16. | Connector seal |
| 17. | Connector seal |
| 18. | Filter holder housing |
| 19. | Front fixing plate with return springs and damper |
| 20. | Attachment nut connection connectors |
| 21. | Holding collar clamp |
| 22. | Circumferential annular gap |
| 23. | Connection, e.g. water supply |
| 24. | Counter bearing and guide plate plunger |
| 25. | Plunger |
| 26. | Connector carrier plate |
| 27. | Connection |
| 28. | Guide pins |
| 29. | Return springs |
| 30. | Rotary shaft for plunger |
| 31. | Upper closure mechanism |
| 32. | Anti-rotation plunger |
| 33. | Connection lever retaining groove |
| 34. | Closure lever |
| 35. | Closure unit |
| 36. | Connection |
| 37. | Connections |
| 38. | Eccentric valve |
| 39. | Valve tappet with seal |
| 40. | Sealing sleeve |
| 41. | Clamping plate |
| 42. | Seal |
| 43. | Lower closure mechanism |
| 44. | Guide groove plunger |
| 45. | Connection e.g. filtrate |
| 46. | Circular pocket |
| 47. | Stop nut |
| 48. | Slanted stop connection connector |
| 49. | Seal groove |
| 50. | |

The invention claimed is:

1. A filter system comprising a filter and a filter holder,
wherein the filter is connected to an upper and a lower filter cap,
wherein on a circumference of each of the filter caps a cross-sectionally T-shaped fixing aid is mounted, having a laterally projecting transverse web, wherein the transverse webs are vertically aligned with each other,
wherein the filter holder comprises a housing and on an outer side of the housing two filter fixings are mounted with grooves in which the transverse webs can be suspended,
wherein four hydraulic connections project laterally from at least one of the filter and the filter caps, the hydraulic connections being vertically aligned with each other,
wherein the filter holder has four connection connectors which are advanced against a spring force by upper and lower closure mechanisms until they engage in an end position in which the connection connectors are tightly connected to the hydraulic connections, and
wherein the upper and lower closure mechanisms apply the spring force in a direction away from the filter when the filter system is assembled.

2. Filter system according to claim 1, wherein the connection connectors in the end position engage around the connections, such that flow cross-section is not reduced.

3. Filter system according claim 1, wherein the filter has two hydraulic connections, and each filter cap has a hydraulic connection.

4. Filter system according to claim 1, wherein each closure mechanism has a rear abutment and guide plate, a front fixing plate and therebetween a sliding connector carrier plate.

5. Filter system according to claim 4, wherein the connection connectors are mechanically connected to the connector carrier plate.

6. Filter system according to claim 4, further comprising return springs that are arranged between the front fixing plate and the connector carrier plate, wherein said springs push away the connector carrier plate from the front fixing plate.

7. Filter system according to claim 4, wherein the abutment and guide plate is provided with at least one plunger sitting on a rotary shaft, by the rotation of which the at least one plunger advances the connector carrier plate against the spring force to the front fixing plate, so that the connector connections abut tightly against the connectors, wherein the at least one plunger engages in the end position.

8. Filter system according to claim 4, wherein the connector carrier plate sits slidably on guide pins.

9. Filter system according to claim 1, wherein on a side of the filter holder, connection levers are arranged, which are rotatably connected to an actuation of at least one plunger with a rotary shaft.

10. Filter system according to claim 1, wherein at least one of the connection connectors is surrounded by an annular gap, such that tolerances can be compensated.

11. A filter system comprising a filter and a filter holder,
wherein the filter is connected to an upper and a lower filter cap,
wherein on a circumference of each of the filter caps a cross-sectionally T-shaped fixing aid is mounted, having a laterally projecting transverse web, wherein the transverse webs are vertically aligned with each other,
wherein the filter holder comprises a housing and on an outer side of the housing two filter fixings are mounted with grooves in which the transverse webs can be suspended,
wherein four hydraulic connections project laterally from at least one of the filter and the filter caps, the hydraulic connections being vertically aligned with each other,
wherein the filter holder has four connection connectors are advanced against a spring force by upper and lower closure mechanisms until they engage in an end position in which the connection connectors are tightly connected to the hydraulic connections,
wherein the connection connectors in the end position engage around the connections, such that flow cross-section is not reduced, and
wherein the spring force acts to bias the connection connectors away from the filter.

12. A filter system comprising a filter and a filter holder,
wherein the filter is connected to an upper and a lower filter cap,
wherein on a circumference of each of the filter caps a cross-sectionally T-shaped fixing aid is mounted, having a laterally projecting transverse web, wherein the transverse webs are vertically aligned with each other, wherein the filter holder comprises a housing and on an outer side of the housing two filter fixings are mounted with grooves in which the transverse webs can be suspended, wherein four hydraulic connections project laterally from at least one of the filter and the filter caps, the hydraulic connections being vertically aligned with each other, wherein the filter holder has four connection connectors which are advanced against a spring force by upper and lower closure mechanisms until they engage in an end position in which the connection connectors are tightly connected to the hydraulic connections, wherein each closure mechanism has a rear abutment and guide plate, a front fixing plate and therebetween a sliding connector carrier plate, wherein the closure mechanisms further comprising return springs that are arranged between the front fixing plate and the connector carrier plate, wherein said springs push away the connector carrier plate from the front fixing plate, thereby applying the spring force in a direction away from the filter when the filter system is assembled.

13. Filter system according to claim 1, wherein the four hydraulic connections project laterally outwardly from the filter and the filter caps.

14. Filter system according to claim 11, wherein the four hydraulic connections project laterally outwardly from the filter and the filter caps.

15. Filter system according to claim 12, wherein the four hydraulic connections project laterally outwardly from the filter and the filter caps.

\* \* \* \* \*